United States Patent [19]

Edwards, Jr. et al.

[11] 4,214,473
[45] Jul. 29, 1980

[54] GASEOUS TRACE IMPURITY ANALYZER AND METHOD

[75] Inventors: David Edwards, Jr., Bellport; William Schneider, Setauket, both of N.Y.

[73] Assignee: The United States of America as represented by the United States Department of Energy, Washington, D.C.

[21] Appl. No.: 970,842

[22] Filed: Dec. 18, 1978

[51] Int. Cl.[2] ............................................. G01N 25/02
[52] U.S. Cl. .................................... 73/23; 73/17 A
[58] Field of Search .................. 13/17 A, 23, 25, 26, 13/29, 17 R, 421.5 R

[56] References Cited

U.S. PATENT DOCUMENTS

| 3,446,056 | 5/1969 | Koch | 73/17 A |
| 3,589,169 | 6/1971 | Lafitte | 73/17 A |

FOREIGN PATENT DOCUMENTS

| 1296726 | 5/1962 | France | 73/17 R |
| 1404573 | 5/1965 | France | 73/23 |
| 327405 | of 1972 | U.S.S.R. | 73/17 R |

*Primary Examiner*—Charles A. Ruehl
*Attorney, Agent, or Firm*—R. V. Lupo; Cornell D. Cornish

[57] ABSTRACT

Simple apparatus for analyzing trace impurities in a gas, such as helium or hydrogen, comprises means for drawing a measured volume of the gas as sample into a heated zone. A segregable portion of the zone is then chilled to condense trace impurities in the gas in the chilled portion. The gas sample is evacuated from the heated zone including the chilled portion. Finally, the chilled portion is warmed to vaporize the condensed impurities in the order of their boiling points. As the temperature of the chilled portion rises, pressure will develop in the evacuated, heated zone by the vaporization of an impurity. The temperature at which the pressure increase occurs identifies that impurity and the pressure increase attained until the vaporization of the next impurity causes a further pressure increase is a measure of the quantity of the preceding impurity.

10 Claims, 2 Drawing Figures

GASEOUS TRACE IMPURITY ANALYZER AND METHOD

BACKGROUND OF THE INVENTION

This invention was made under, or during the course of, a contract with the U.S. Department of Energy.

Cryogenic gases, herein defined as those liquefiable at temperatures below −100° C., such as argon, hydrogen and helium, are used in processes requiring the gas to be in a highly purified form. For such processes, it is necessary to analyze the gas to determine the presence of even trace impurities and the quantity of each such impurity.

While several analytical techniques are known for identifying and quantifying each impurity in a cryogenic gas, the known techniques require expensive apparatus and instrumentation. Additionally, such prior techniques are often time-consuming and involve operation by a skilled technician.

With the growing diversity of processes which depend on the use of a gas of very high purity, there is a real need for a simple analyzer for trace impurities which is easy and rapid in operation.

It is an object of this invention to provide a simple and relatively inexpensive apparatus for measuring the content of trace impurities in a gas.

A further object is to provide such apparatus which does not require a specially trained operator.

Still another object is to provide such apparatus which permits the rapid analysis of the trace impurities.

SUMMARY OF THE INVENTION

In accordance with this invention, a predetermined volume of gas is drawn as sample into an evacuated, heated zone maintained at a selected temperature which prevents the condensation or deposition of any impurity in the gas on the walls of the heated zone. When the heated zone has been filled with the gas sample, the zone is sealed to prevent the flow of gas either into or out of the zone. A small segregable portion of the heated zone is now chilled to a very low temperature selected to condense all the impurities in the gas sample in the chilled portion. When all the impurities have been deposited in the chilled portion, the residual gas from which the impurities have been removed is discarded by evacuation from the heated zone including the chilled portion. The evacuated, heated zone is again sealed and the chilled portion is gradually warmed to vaporize the impurities deposited therein in the order of their increasing boiling points. As the chilled portion is warmed, the temperature thereof which causes the pressure to rise in the heated zone because of the vaporization of an impurity serves to identify that impurity. The maximum pressure developed in the heated zone by the vaporization of the impurity provides a measure of the quantity of that impurity.

When the pressure in the heated zone again shows an increase with the increasing temperature of the small, chilled portion, the vaporization and desorption of another impurity is signalled. The temperature of the chilled portion causing the new pressure increase identifies this other impurity while the new pressure increase provides a measure of the quantity of this other impurity. Any further increase of the pressure in the heated zone with the increasing temperature of the chilled portion signals the desorption of still another impurity. The temperature of the small, chilled portion at which a pressure increase occurs again identifies the additional impurity while the maximum pressure caused by the vaporization of that impurity provides a measure of its quantity.

The cryogenic gases which can be advantageously analyzed in accordance with this invention have been defined as those that are liquefiable at temperatures below −100° C. Such gases include argon, neon, krypton, xenon, oxygen, nitrogen, hydrogen and helium.

The temperature at which the heated zone is uniformly maintained is selected high enough to prevent sorption or condensation on the walls of the zone of any impurity in the gas to be analyzed. In most cases, a temperature of about 200° C. is adequate. Similarly, the temperature to which the segregable portion of the zone is chilled is chosen low enough to condense or adsorb all of the impurities in the gas to be analyzed. In most cases, chilling to a temperature below −150° C. is adequate and may be conveniently achieved by contacting the exterior surface of the segregable portion of the zone with a readily available liquefied gas such as methane, air, oxygen or nitrogen. On the basis of safety, economy and low boiling point, liquid nitrogen is a preferred coolant.

When the cryogenic gas to be analyzed contains trace amounts of other cryogenic gases as impurities, an appropriate adsorbent such as activated carbon or a molecular sieve is placed in the segregable portion of the heated zone so that upon chilling the adsorbent will capture the impurities and thus effect separation from the gas undergoing analysis. For instance, helium or hydrogen containing oxygen and nitrogen as impurities would be analyzed pursuant to this invention in a heated zone having a segregable portion which contains a suitable adsorbent for the impurities. The chilling of the portion containing the adsorbent to deposit the gaseous impurities thereon, the evacuation of the heated zone including the chilled portion and the warming of the chilled portion to effect desorption of the impurities captured by the adsorbent would be carried out in the same manner that has been described for this sequence of steps when the segregable portion of the heated zone does not contain an adsorbent. Again, during warming, the temperature of the segregable portion of the heated zone at which an impurity is desorbed from the adsorbent identifies the impurity while the maximum pressure increase in the heated zone arising from the desorption of that impurity provides a measure of its quantity.

Common impurities in cryogenic gases include moisture, carbon monoxide, carbon dioxide, hydrogen sulfide, ammonia and hydrocarbons which are often present in high pressure gases that have been contaminated by the oil lubricant in the compressor used to raise the pressure of the gases. Hydrocarbons present as impurities in a gas are generally referred to collectively as oil.

The zone of predetermined volume in which the gas analysis is carried out in accordance with this invention is provided by a metal vessel which has an inner surface substantially free of any roughness that might tend to cause sorption of the gas or its impurities thereon. Aluminum, brass and stainless steel are metals well suited for the fabrication of the vessel used for the gas analysis of this invention.

In most instances, the types of impurities in a cryogenic gas are known or at least suspected. Each impurity has a characteristic vaporization or desorption temperature. Hence, before using the heated, evacuated zone of this invention to analyze a cryogenic gas for impurities, it can be used to determine the characteristic desorption temperature of a selected impurity which has been added to the purified cryogenic gas. Following the procedure of this invention with the cryogenic gas containing the known added impurity, during the warming of the small, chilled portion of the heated, evacuated zone a pressure increase will occur at a certain temperature and that temperature is the characteristic desorption temperature of that impurity.

The characteristic desorption temperature of another selected impurity can be determined in the same manner by adding the impurity to the purified gas and following the procedure of the invention to find at what temperature this other impurity will be desorbed and cause a pressure rise in the heated zone.

The same procedure can be repeated for each known or suspected impurity in the cryogenic gas to establish the characteristic vaporization or desorption temperature of each impurity. When the characteristic desorption temperatures have been determined for all of the impurities, the analysis of the cryogenic gas containing naturally present impurities can be carried out pursuant to this invention.

While the determination of the characteristic vaporization temperature of each impurity has just been described by adding a single impurity to the pure cryogenic gas, it is also possible to add several different impurities to the pure gas and sequentially determining the characteristic vaporization temperatures of all the added impurities in a single operation of the previously described procedure. For instance, if a cryogenic gas is known to contain ammonia, moisture and oil as naturally present impurities, all three impurities can be added to the gas in pure form to establish sequentially the characteristic desorption temperature of each impurity because as the chilled portion of the heated, evacuated zone is warmed the impurities will be desorbed in the order of their increasing boiling points, that is, in the order of ammonia, moisture and oil. Hence, when the first pressure rise in the heated zone is noted, the temperature of the chilled portion at that time is the characteristic desorption temperature for ammonia. As the chilled zone is warmed further, the next pressure increase indicates the desorption of moisture and at that point the characteristic desorption temperature of water corresponds to the temperature of the chilled portion. When the next pressure increase occurs, the temperature of the chilled portion will correspond to the characteristic desorption temperature for oil.

BRIEF DESCRIPTION OF THE DRAWINGS

Further clarification of the invention will become apparent from the following description which is presented in relation to the accompanying drawings of which.

DESCRIPTION OF A PREFERRED EMBODIMENT

Figure 1:
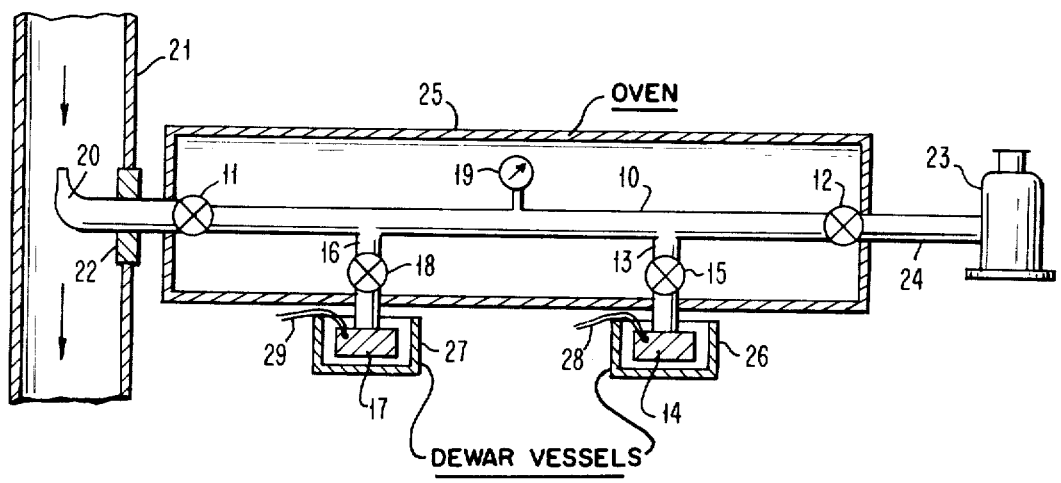
FIG. 1 is a diagrammatic representation of a preferred apparatus of the invention.

The apparatus of FIG. 1 comprises tubular manifold 10 having inlet valve 11 at one end and outlet valve 12 at the opposite end. Branch 13 of manifold 10 terminates in sealed container 14. Valve 15 in branch 13 is used to control the flow of gas into and out of container 14. Branch 16 of manifold 10 also terminates in sealed container 17. Valve 18 in branch 16 is used to control the flow of gas into and out of container 17. Pressure gauge 19 is connected to manifold 10. Sampling tube 20 connected to inlet valve 11 extends into pipe line 21. To prevent the deposition of impurities from the gas sample within tube 20, heating means, such as a winding of electrical heating tape (not shown), is used to keep tube 20 at a temperature of about 200° C. Preferably, thermal isolator 22 surrounds tube 20 and provides the seal between tube 20 and pipe line 21. Outlet valve 12 is connected to vacuum pump 23 by tube 24. Oven 25 encloses manifold 10 including valves 11, 12, 15, 18. Dewar vessel 26 into which liquefied gas can be poured surrounds small container 14 and Dewar vessel 27 similarly surrounds small container 17.

Operation of the apparatus of FIG. 1 will now be described in an illustrative example of the invention involving the analysis of high pressure helium containing ammonia, moisture and oil as trace impurities.

Oven 25 is maintained at a temperature of 200° C. so that manifold 10 with branches 13, 16, valves 11, 12, 15, 18 and pressure gauge 19 are all at that temperature. With inlet valve 11 closed and valves 12, 15, 18 open, vacuum pump 23 is operated to evacuate manifold 10, branches 13, 16 and containers 14, 17 to a pressure of about 1 micron (0.001 millimeter) of Hg (mercury). During the evacuation period, containers 14 and 17 are also heated in any convenient manner to a temperature of 200° C.

When manifold 10 has been evacuated, valves 12, 18 are closed and then inlet valve 11 is opened so that the impure helium at an absolute pressure of 15 atmospheres in pipe line 21 flows through sampling tube 20 to fill manifold 10 and container 14. Valve 11 is again closed and the heating of containers 14, 17 is stopped. Subsequently, vessel 26 is filled with liquid nitrogen to chill container 14 to a temperature of about $-195°$ C. Thereupon all the impurities in the helium sample within manifold 10 are condensed and deposited in container 14. Outlet valve 12 is now opened to remove the residual purified helium from manifold 10 and container 14 by way of tube 24 and vacuum pump 23. When the pressure in manifold 10 is again down to about 1 micron of Hg, valve 12 is closed.

Vessel 26 containing liquid nitrogen is then removed and container 14 is allowed to warm gradually. Pressure readings of gauge 19 are recorded together with simultaneous temperature readings made with thermocouple 28 attached to container 14 during the warming of chilled container 14.

Figure 2:
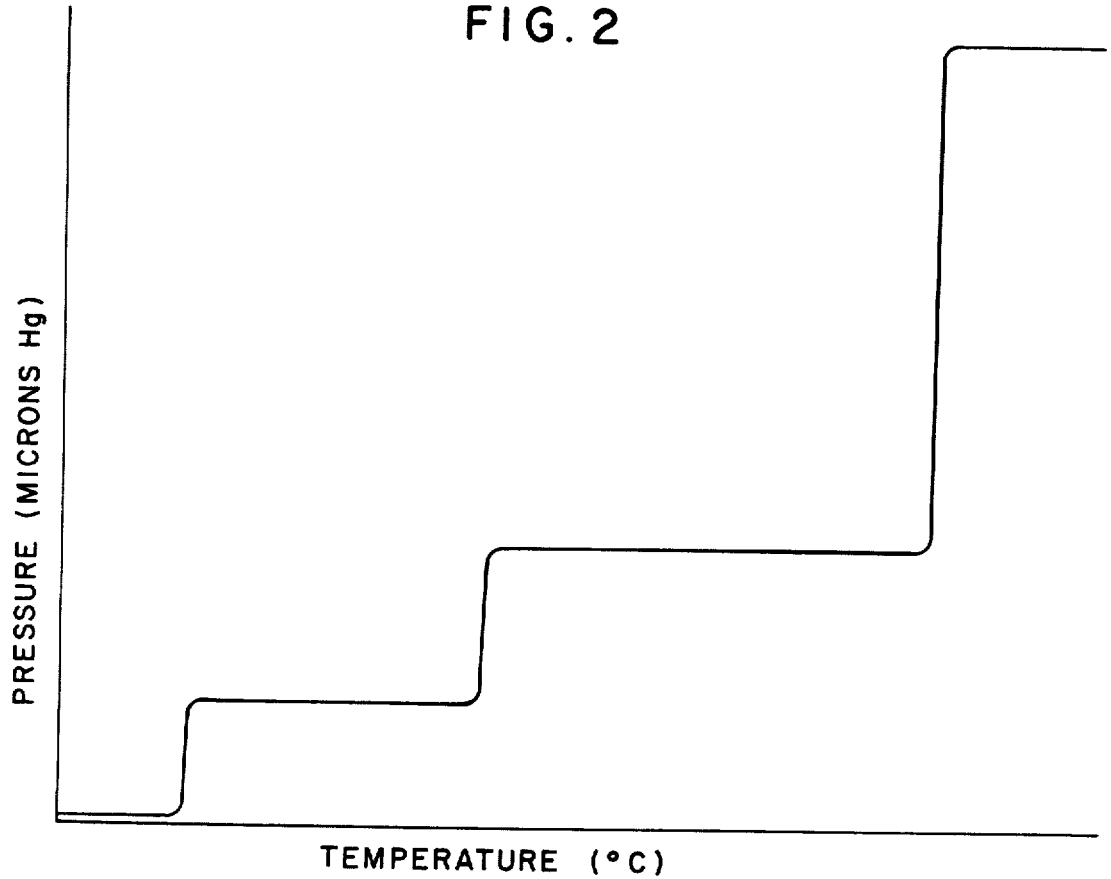
FIG. 2 is a graph showing pressure increases in the apparatus as the temperature of the chilled portion thereof is raised to vaporize the impurities originally in a gas which have been removed from that gas by deposition in the chilled portion of the apparatus pursuant to this invention.

FIG. 2 is the type of graph formed by plotting the simultaneous readings of pressure and temperature made with gauge 19 and thermocouple 28, respectively. From the graph it was determined that at a temperature of about $-152.5°$ C. the first desorption of an impurity was signalled by the rapid increase of pressure. Prior tests made with pure helium to which ammonia had been added as impurity and conducted as hereinbefore disclosed had established that $-152.5°$ C. is the characteristic desorption temperature of ammonia. Such prior tests with moisture and oil as impurities in pure helium had established that the temperatures of $-33°$ C. and $129.5°$ C. are the characteristic desorption temperatures of moisture and oil, respectively. Hence, the second sharp pressure increase in the graph at a temperature of $-33°$ C. was evidence of the vaporization of moisture in container 14 while the further pressure jump at a temperature of $129.5°$ C. indicated the desorption of oil in container 14.

The actual pressure increase caused by each of the impurities is a measure of the quantity of that impurity originally present in the helium sample. The pressure increases in the graph for ammonia, moisture and oil were 30, 53 and 170 microns of Hg, respectively.

Inasmuch as the helium sample drawn into the apparatus of this invention was at an absolute pressure of 15 atmospheres ($15 \times 760 \times 1000 = 1.14 \times 10^7$ microns of Hg) the quantity of each impurity can be computed from the pressure increase in microns of Hg shown in the graph, thus:

$$\text{Ammonia} = 30/(1.14 \times 10^7) = 2.63 \times 10^{-6} \text{ or approximately 3 ppm}$$

$$\text{Water} = 53/(1.14 \times 10^7) = 4.64 \times 10^{-6} \text{ or approximately 5 ppm}$$

$$\text{Oil} = 170/(1.14 \times 10^7) = 1.49 \times 10^{-5} \text{ or approximately 15 ppm}$$

The illustrative analysis of the helium sample conducted in accordance with the invention reveals that the impurities: ammonia, moisture and oil were present in the quantities of approximately 3, 5 and 15 parts per million (ppm), respectively.

If the helium sample had contained oxygen and nitrogen as the only impurities, the analytical procedure of the preceding illustrative example would have been carried out by using container 17 instead of container 14. Liquid nitrogen is not cold enough to condense oxygen and nitrogen in container 14. For this reason, container 17 holds a layer of adsorbent, such as activated carbon or a molecular sieve, capable of capturing oxygen and nitrogen when the adsorbent is chilled by filling vessel 27 with liquid nitrogen. To use container 17 instead of container 14, after the apparatus had been evacuated by vacuum pump 23 and valve 12 has been closed, valve 15 would also be closed whereas in the preceding example valve 18 was closed. Thus, when valve 11 is opened to fill the apparatus with the helium sample, container 17 will also be filled. Thereafter, the previously described procedure to deposit ammonia, moisture and oil in container 14 and then to desorb these impurities in the order of their increasing boiling points is followed to deposit nitrogen and oxygen on the adsorbent in container 17 and then to desorb these impurities in the order of their increasing boiling points.

During the warming of container 17, simultaneous readings made with pressure gauge 19 and thermocouple 29 will provide the data for plotting a graph similar to that of FIG. 2. Of course, the characteristic desorption temperatures for nitrogen and oxygen will be different from those for ammonia, moisture and oil. Again, by examining the graph, the pressure increases resulting from the desorption of nitrogen and oxygen can be used to compute the content of each of these impurities in the helium as has been previously described.

Assuming the helium sample contained all five impurities previously mentioned, the procedure followed in the preceding illustrative example would be modified as follows. After container 14 is chilled to deposit ammonia, moisture and oil in container 14, valve 18 is opened and container 17 is chilled with liquid nitrogen so that nitrogen and oxygen in the helium sample are adsorbed in container 17. Thereafter, valve 12 is opened to evacuate the apparatus. Then, valves 12, 18 are closed and the desorption of the impurities in container 14 is carried out in the manner previously described. When the desorption of the impurities in container 14 is completed, valve 12 is opened to evacuate the apparatus. As soon as the apparatus has been evacuated, valves 12, 15 are closed and valve 18 is opened. Now the desorption of nitrogen and oxygen is carried out by warming container 17 in the manner already described.

Thus, a single sample of helium drawn into manifold 10 can be analyzed for all five impurities by first depositing ammonia, moisture and oil in container 14 and then depositing nitrogen and oxygen in container 17. While desorption of the impurities in container 14 has been described as preceding the desorption of the impurities in container 17, the desorption of the impurities in container 17 can be carried out first.

Branches 13, 16 of the apparatus terminate in containers 14, 17, respectively. The term, container, has been used in its broadest sense because numerals 14, 17 are applied to solid blocks of metal welded or otherwise attached to the ends of branches 13, 16, respectively. When blocks 14, 17 are immersed in liquid nitrogen or other coolant, the impurities in the gas sample are deposited on the portion of the surface of each block that seals the end of the branch to which that block is attached.

The apparatus of this invention can also be used to determine the heats of vaporization of various substances, such as acetone, methanol and carbon dioxide. In such case, during the warming of a chilled container, instead of reading the pressure, the change of pressure per unit of time, for example, the increment of pressure rise per 10 seconds, is recorded. When such data are plotted against the corresponding temperatures of the container being warmed, the graph takes the form of a curve that rises sharply, reaches a peak and drops off substantially vertically. Knowing the temperature at which the peak occurs and the width of the peak, the heat of vaporization of the substance can be calculated using a known formula.

Therefore, if the apparatus of the invention is used to analyze a gas containing an unknown impurity suspected to be one of several different substances, the heat of vaporization of that impurity calculated from the peak temperature and peak width can be compared with the published heats of vaporization of the several known substances. The known heat of vaporization of a given substance which substantially equals the heat of vaporization of the impurity originally present in the gas serves to identify what the impurity is.

The small portion of the zone of predetermined volume used pursuant to this invention to collect the trace impurities in the gas sample is generally not more than 5% and often preferably not more than 2% of that predetermined volume. Because containers 14, 17 are volumetrically small relative to the volume of the apparatus of FIG. 1, the small quantity of each impurity which is vaporized while a container is being warmed attains the temperature of the apparatus within oven 25 extremely rapidly. Hence, the desorbed impurity is substantially instantaneously in thermal equilibrium with manifold 10 which is held at a constant temperature when its pressure is measured by gauge 19 connected to manifold 10.

Those skilled in the art will visualize variations of the invention without departing from its spirit and scope. Accordingly, only such limitations should be imposed on the scope of the invention as are set forth in the appended claims.

What is claimed is:

1. A process of analyzing a cryogenic gas for trace impurities which comprises drawing a sample of said gas of predetermined volume into a heated, evacuated zone maintained at an elevated temperature selected to prevent condensation of any impurity in said zone, chilling a small portion of said zone to a low temperature selected to condense trace impurities in said sample in said chilled portion, re-evacuating the residual gas of said sample from said zone, gradually warming said chilled portion to effect vaporization of condensed impurities in the order of their increasing boiling points in said re-evacuated zone, measuring the warming temperature of said chilled portion each time that a pressure increase is measured in said re-evacuated zone, identifying each vaporized impurity by comparing the temperature of said chilled portion measured when each vaporized impurity caused a pressure increase with the temperatures of said chilled portion previously determined to cause vaporization of known impurities, and calculating the amount of each vaporized impurity in said gas from the ratio of the pressure increase caused by each vaporized impurity to the pressure of said sample of said gas drawn into said zone.

2. The process of claim 1 wherein the elevated temperature of the evacuated zone is about 200° C. and the temperature of the chilled portion is about −195° C.

3. The process of claim 2 wherein the sample of cryogenic gas is helium at an elevated pressure.

4. The process of claim 1 wherein the chilled portion contains an adsorbent for trace impurities in the cryogenic gas.

5. The process of claim 1 wherein the evacuated zone has an adsorbent-containing second small portion that is segregated prior to drawing the sample of cryogenic gas into said zone, after impurities have been condensed in the chilled portion opening said second portion to said zone, chilling said second portion to a low temperature to adsorb uncondensed impurities on said adsorbent, again segregating said second portion, after impurities condensed in said chilled portion have been vaporized to identify each vaporized impurity and calculate its amount in said gas again re-evacuating said zone, again opening said second portion to said zone, and warming said second portion to desorb impurities from said adsorbent in the order of their boiling points so as to identify each desorbed impurity and calculate its amount in said gas.

6. The process of claim 5 wherein both small portions of the evacuated zone are chilled by contact with liquid nitrogen.

7. Apparatus for analyzing a cryogenic gas for trace impurities which comprises a metal vessel having a small branch portion which can be chilled to a low temperature while said vessel is heated uniformly to an elevated temperature by heating means, means for evacuating said vessel, means for introducing a sample of said gas into said vessel, means for chilling and then gradually warming said branch portion, a pressure gauge for measuring the pressure in said vessel, and a temperature gauge for measuring the temperature of said branch portion during the gradual warming thereof.

8. The apparatus of claim 7 wherein the small branch portion of the metal vessel comprises a solid metal block attached thereto.

9. The apparatus of claim 7 wherein the metal vessel has a second small branch portion which can be chilled to a low temperature and said second branch portion has valve means for segregating said second branch portion from said vessel.

10. The apparatus of claim 9 wherein each of the small branch portions of the metal vessel comprises a solid metal block attached thereto.

* * * * *